United States Patent [19]
Feustel et al.

[11] Patent Number: 5,908,582
[45] Date of Patent: Jun. 1, 1999

[54] LIQUID FORMULATIONS CONTAINING SULFOSUCCINIC ACID DIESTER

[75] Inventors: Dieter Feustel, Monheim; Uwe Held, Velbert; Joachim Meyer, Hilden, all of Germany

[73] Assignee: Henkel Kommanditgesellschaft auf Aktien, Duesseldorf, Germany

[21] Appl. No.: 08/592,391

[22] PCT Filed: Jul. 25, 1994

[86] PCT No.: PCT/EP94/02450

§ 371 Date: Feb. 1, 1996

§ 102(e) Date: Feb. 1, 1996

[87] PCT Pub. No.: WO95/04035

PCT Pub. Date: Feb. 9, 1995

[30] Foreign Application Priority Data

Aug. 2, 1993 [DE] Germany ............... 43 25 923

[51] Int. Cl.$^6$ ............... B01F 17/00; C11D 1/00; C11D 10/00
[52] U.S. Cl. ............... 252/354; 510/537
[58] Field of Search ............... 560/149, 150; 106/23, 20; 510/537; 252/354

[56] References Cited

U.S. PATENT DOCUMENTS

| | | | |
|---|---|---|---|
| 2,028,091 | 1/1936 | Jaeger | 260/106 |
| 2,176,423 | 10/1939 | Jaeger | 260/481 |
| 2,416,254 | 2/1947 | Gilbert | 117/165 |
| 2,879,214 | 3/1959 | Divine | 204/158 |
| 3,998,762 | 12/1976 | Murata et al. | 252/551 |
| 4,384,978 | 5/1983 | Ploog et al. | 252/353 |
| 4,476,037 | 10/1984 | Ploog et al. | 252/353 |
| 5,098,478 | 3/1992 | Krishnan et al. | 106/23 |

FOREIGN PATENT DOCUMENTS

| | | |
|---|---|---|
| 266815 B1 | 12/1990 | Czech Rep. . |
| 0024711 | 3/1981 | European Pat. Off. . |
| 1573080 | 12/1968 | France . |
| 2551111 | 5/1976 | Germany . |
| 62-209200 A2 | 9/1987 | Japan . |
| 760121 | 10/1956 | United Kingdom . |
| 1050578 | 12/1966 | United Kingdom . |

OTHER PUBLICATIONS

Anionic Surfactants, Part II, W.M. Linfield,M. Dekker, 1976, pp. 406 et seq.

Handbook of Surfactants, M. R. Porter, Blackie, 1991, pp. 107 et seq.

Ullmanns Encyclopädiemder technischen Chemie, 4th Edition, (1980), vol. 19, pp. 31 et seq.

Römpp,Chemie Lexikon, 9 th Edition (1991), vol. 4, p. 2617.

*Primary Examiner*—Jose' G. Dees
*Assistant Examiner*—Alton Pryor
*Attorney, Agent, or Firm*—Ernest G. Szoke; Wayne C. Jaeschke; Henry E. Millson, Jr.

[57] ABSTRACT

A liquid composition comprising

A) at least one sulosuccinic acid diester of the formula:

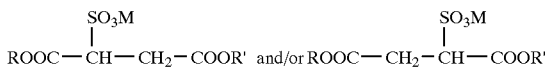

in which M is an inorganic or organic cation, R and R' independently of one another represent aliphatic or cycloaliphatic $C_{3-22}$ alkyl, $C_{2-22}$ alkenyl or optionally $C_{1-8}$ alkyl-substituted $C_{6-22}$ aryl;

B) water as a solvent; and

C) a cosolvent consisting essentially of at least one polymer containing alkylene oxide units which is liquid at 10° C.

27 Claims, No Drawings

LIQUID FORMULATIONS CONTAINING SULFOSUCCINIC ACID DIESTER

This application is a 371 of PCT/EP 94/02450 filed Jul. 25, 1994.

BACKGROUND OF THE INVENTION

1. Field of the Invention

This invention relates to liquid formulations containing a sulfosuccinic acid diester, to a process for their production and to the use of these liquid formulations as wetting agents and emulsifiers.

2. Statement of Related Art

Diesters of sulfosuccinic acid have been known for many years as effective wetting agents. In the course of the changeover from systems containing organic solvents to water-based systems, this class of compounds has acquired increasing significance. The synthesis of the diesters would appear at first glance to be very simple, as reflected in early patent literature. Thus, U.S. Pat. No. 2,176,432, U.S. Pat. No. 2,416,254 and U.S. Pat. No. 2,028,091 describe the production of sulfosuccinic acid diesters by methods which cannot be carried out on an industrial scale and which are not economically justifiable.

GB-PS 1,050,578, FR-PS 1 573 080, GB-PS 760,121 and U.S. Pat. No. 2,879,214 describe the production of liquid formulations of sulfosuccinic acid diesters on an industrial scale. However, it is clear from these documents that the reaction is characterized by several special features and that controlled measures have to be taken to influence the reaction. It is less the synthesis of the maleic acid diesters which are used as raw materials in the synthesis of sulfosuccinic acid diesters than the sulfitation of this raw material to the sulfonated component which is regarded as problematical. A review of the sulfitation of maleic acid diesters can be found in Anionic surfactants, Part II, W. M. Linfield, M. Dekker, 1976, pages 406 et seq. and in Handbook of surfactants, M. R. Porter, Blackie, 1991, pages 107 et seq.

It is clear from the literature that the problem with sulfitation lies in the reaction of a hydrophobic diester with a water-soluble $HSO_{3-}$ and in the formation of gel phases. According to various references, the reaction is very slow and, after an initial phase, is clearly exothermic and difficult to control. To be able to carry out the reaction, it is recommended in GB-PS 1,050,578 to use an initiator. The initiator may be a surfactant, more particularly the sulfosuccinic acid diester to be produced, or a solvent, such as ethanol. At the same time, an organic solvent, such as mineral oil, white oil, paraffin or an aromatic solvent, is used. FR-PS 1 573 080 describes the addition of the sulfite solution to enable the exothermic nature of the reaction to be better controlled. This document also mentions the possibility of carrying out the reaction under pressure which allows reaction temperatures above the boiling point of the mixture and prevents the loss of sulfite through evaporation tion of $SO_2$. A short reaction time is mentioned as an advantage. U.S. Pat. No. 2,879,214 recommends the exposure of the reaction mixture to UV light to accelerate the reactions. The use of ethanol is described explicitly or without any particular references in FR-PS 1 573 080, in GB-PS 760,121 and in U.S. Pat. No. 2,879,214.

DESCRIPTION OF THE INVENTION

Experience has shown that the use of volatile organic solvents or solubilizers, such as ethanol, is necessary to guarantee a rapid and controllable sulfitation reaction. In addition, solvents are required to formulate highly concentrated, liquid sulfosuccinic acid diester formulations. The diesters of sulfosuccinic acid show poor solubility in water and, in addition, form gel phases in the medium concentration range. Through the addition of co-solvents, the liquid formulations of sulfosuccinic acid diesters remain homogeneous and liquid which affords clear handling advantages.

On the other hand, the presence of solvents is undesirable in terms of emission and the flashpoint. The development of solventless systems in the paint and lacquer field is increasingly focusing on low VOC (volatile organic components) contents. A high flashpoint is of advantage in terms of production, storage and transport.

Accordingly, a first problem addressed by the present invention was to provide liquid, homogeneous, clear formulations containing a sulfosuccinic acid diester which would contain solvents with a high flashpoint or no flashpoint. Flashpoints of at least 55° C. are regarded as high in the context of the present invention. In addition, the liquid formulations would be stable in storage and easy to handle.

According to the invention, this problem has been solved by liquid formulations containing a sulfosuccinic acid diester corresponding to the following general formulae:

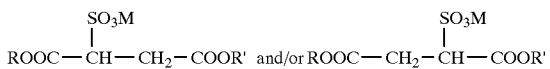

in which M is an inorganic or organic cation, R and R' independently of one another represent aliphatic or cycloaliphatic $C_{3-22}$ alkyl, $C_{2-22}$ alkenyl or optionally $C_{1-8}$ alkyl-substituted $C_{6-22}$ aryl, in water as solvent and a co-solvent, characterized in that the co-solvent is a polymer containing alkylene oxide units which is liquid at 10° C.

According to the invention, R and R' independently of one another may be selected from $(CH_3)_2CH—$, $C_4H_9—$, $C_2H_5CH(CH_3)—$, $C_5H_{11}—$, $C_3H_7CH(CH_3)—$, $C_6H_{13}—$, $C_4H_9CH(C_2H_5)CH_2—$, $C_8H_{17}—$, $C_6H_{13}CH(CH_3)—$, $C_7H_{15}CH(CH_3)—$, $C_5H_{11}CH(C_2H_5)CH_2—$, $CH_3C(CH_3)_2CH_2CH(CH_3)CH_2CH_2—$, $C_{10}H_{21}—$, $C_8H_{17}CH(CH_3)—$, $(C_4H_9)_2CHCH_2—$, $CH_3CH(CH_3)—(CH_2)_3—CH(CH_3)(CH_2)_2—$, $C_4H_9CH(C_2H_5)—CH_2CH_2CH(CH_3)—$, $C_{12}H_{25}—$, $C_6H_{13}CH(C_4H_9)CH_2—$, $(CH_3)_2CHCH_2CH(CH_3CH_2—CHCH_2CH(CH_3)_2)_2—$, $C_{13}H_{27}—$, $C_4H_9CH(C_2H_5)CH_2CH=CHCH_2CH(CH_3)CH_2—$, $C_{18}H_{37}—$, $C_8H_{17}CH=CHC_8H_{16}—$, $p$-$(CH_3)_3C$-$CyClo$-$C_6H_{10}—$, $p$-$(C_2H_5C—(CH_3)_2$-$CyClo$-$C_6H_{10}—$, $p$-$C_4H_9CH(CH_3)$-$cyclo$-$C_6H_{10}CH_2—$, $CH_3C_6H_4—$.

Peferred cations M are those of the alkali metals, more particularly lithium, sodium, potassium.

Suitable organic cations are those which contain a quaternary nitrogen atom, such as in particular ammonium.

The co-solvents for the sulfosuccinic acid diesters are preferably block polymers of ethylene oxide (EO) and propylene oxide (PO) which contain at least 20 mole-% of EO. The percentage content of PO may be 90 mole-%, but is preferably between 50 and 80 mole-%. The number average molecular weight of these EO/PO block polymers is between 500 and 20,000 and preferably between 500 and 5,00. Block polymers such as these and their production are known from the prior art. However, further relevant particulars can be found in Ullmanns Encyklopädie der technischen Chemie, 4th Edition, (1980), Vol. 19, pages 31 et seq.

The block polymers of EO and PO may be additionally esterified or etherified. Suitable ester/ether groups contain 1 to 22 carbon atoms and may be linear, branched or cyclic. However, the ethanoic, propanoic and butanoic acid esters or the methyl, ethyl, propyl, isopropyl, butyl, isobutyl or tert-.butyl ethers of the block polymers are preferred. End capping processes based on etherification or esterification are known to the expert from the literature.

The liquid polymer containing alkylene oxide units which is suitable as co-solvent for the sulfosuccinic acid diesters may be selected from addition products of EO and/or PO with monofunctional or polyfunctional alcohols. The polyfunctional alcohols in turn may be selected in particular from ethylene glycol, propylene glycol, glycerol, polyethylene glycol (PEG) and polypropylene glycol (PPG).

In general, the liquid formulation according to the invention is characterized in that the liquid polymer is present in the formulation in a quantity of 1 to 40% by weight and preferably 5 to 20% by weight, based on the sulfosuccinic acid diester, and in that the sulfosuccinic acid diester is present in the mixture of water and the liquid polymer in a quantity of up to 70% by weight and preferably in a quantity of 30 to 60% by weight.

Particularly preferred liquid formulations according to the invention contain didecyl sulfosuccinate, diisodecyl sulfosuccinate, di-2-ethylhexyl sulfosuccinate or diisotridecyl sulfosuccinate as sulfosuccinic acid diesters. The preferred cation is the sodium cation.

Corresponding formulations according to the invention have a high flashpoint or no flashpoint and are homogeneous, clear and easy to handle. In addition, they are distinguished by very high stability in storage. This stability in storage is reflected in particular in the fact that no skin is formed on the solution in storage through the evaporation of lower alcohols.

As already mentioned, the production of the diesters of sulfosuccinic acid is not without problems and, in the case of groups R and R' containing 3 to 8 carbon atoms, leads to the formation of gel phases during cooling to room temperature where water is used as the sole solvent. In the case of groups R and R' containing 9 to 22 carbon atoms, gel phases are actually formed during the reaction at elevated temperature where water is used as the sole solvent. Accordingly, the reaction has hitherto been carried out in the presence of lower alcohols, more particularly ethanol or isopropanol, as co-solvent so that the formation of gel phases can be very largely avoided.

In view of the need to avoid liquid organic solvents even in formulations and to use solvents with a high flashpoint or no flashpoint during the actual production process, another problem addressed by the present invention was to provide a practicable process for the production of the formulations according to the invention which would make it possible directly to produce the liquid formulations of sulfosuccinic acid diesters according to the invention which would not show any tendency towards gel formation either during the reaction of the starting compounds to the sulfosuccinates or during cooling of the reaction mixture to room temperature.

According to the invention, this problem has been solved by a process for the production of the above-described liquid formulations containing sulfosuccinic acid diester from a maleic acid diester corresponding to the general formula ROOC—CH=CH—COOR', where R and R' independently of one another represent aliphatic or cycloaliphatic $C_{3-22}$ alkyl, $C_{2-22}$ alkenyl or optionally $C_{1-8}$-alkyl-substituted $C_{6-22}$ aryl, and a suitable sulfiting agent in water as solvent in the presence of a liquid water-soluble co-solvent at temperatures of 60 to 150° C. and optionally under excess pressure; where R and R' represent $C_{3-8}$ alkyl, the co-solvent may be added to the reaction mixture after the sulfitation reaction and before cooling.

The diesters with short-chain alcohols containing up to 8 carbon atoms, such as isobutanol, isoamyl alcohol or 2-ethyl hexanol, may be synthesized in the absence of a co-solvent under suitable reaction conditions However, in order to obtain homogeneous and liquid products and to avoid the formation of gel phases, even during cooling of the reaction mixture to room temperature, it is necessary to use the co-solvents according to the invention. However, the sulfosuccinic acid diesters of the relatively long-chain alcohols containing 9 to 22 carbon atoms are actually produced in the presence of the liquid cosolvents because the formation of gel phases cannot be avoided, even at elevated reaction temperatures, where water is used as the sole solvent.

So far as the liquid polymers to be used as co-solvents in accordance with the invention are concerned, reference is made to the foregoing observations.

In the maleic acid diesters to be used in accordance with the invention corresponding to the formula ROOC—CH=CH—COOR', R and R' have the meanings defined above. These maleic acid diesters are prepared by methods known from the prior art, cf. Römpp, Chemie Lexikon 9th Edition (1991), Vol. 4, page 2617 and the literature cited therein.

The sulfiting agents are agents typically used in sulfiting reactions, more particularly $MHSO_3$, $M_2SO_3$ or $M_2S_2O_5$, where M is an inorganic or organic cation as described above.

The molar ratio of maleic acid diester to the sulfiting agent (based on $HSO_3^-$) is between 1:0.9 and 1:2, preferably between 1:1 and 1:1.5 and more preferably between 1:1 and 1:1.2.

The reaction temperature is preferably between 60 and 150° C. Where higher reaction temperatures than 100° C. are to be applied, the reaction has to be carried out under excess pressure in suitable reactors The upper limit to the reaction temperature is imposed by the isomerization temperature of maleic acid to fumaric acid which is of the order of 150° C.

It has also been found that it can be of advantage to carry out the sulfitation reaction of the maleic acid diester in the presence of a surfactant, preferably the sulfosuccinic acid diester salt to be produced, as initiator The effect of this is that the reaction is easier to control from the outset because otherwise it only starts after a certain-time as a result of auto-catalysis. The initiator may be added to the reaction mixture in a quantity of 0.1 to 20% by weight and preferably in a quantity of 0.1 to 15% by weight, based on the maleic acid diester.

To carry out the reaction, the percentage of water and co-solvent in the reaction mixture is gauged in such a way that the liquid polymer is used in a quantity of 1 to 40% by weight and preferably 5 to 20% by weight, based on the required sulfosuccinic acid diester reaction product. For practical applications, it is best to adapt the percentages of water and co-solvent to one another in such a way that the required sulfosuccinic acid diester is present in the solvent/co-solvent mixture in the form of an up to 70% by weight solution and preferably a 30 to 60% by weight solution.

The process mentioned above has the overall advantage that it can always be carried out in a clear and homogeneous solution without any need to use volatile organic solvents with a low flashpoint. The formation of gel phases can be completely avoided in this way.

The liquid formulations according to the invention are used in particular as wetting agents and emulsifiers. The liquid formulations according to the invention are distinguished in particular by their compatibility where they are used as wetting agents in polymer dispersions This is reflected above all in the fact that, in particular, the sulfosuccinic acid diesters of relatively long-chain ester groups containing more than 8 carbon atoms do not lead to clouding through precipitation in use.

Basically, however, the liquid formulations according to the invention are suitable for a range of typical applications as listed in particular in U.S. Pat. No. 2,176,423. However, the formulations according to the invention are preferably used in water-based paints, printing inks and overprinting lacquers.

The following Examples are intended to illustrate the invention without limiting it in any way.

EXAMPLES

Example 1

Synthesis of di-2-ethylhexyl sulfosuccinate 295.5 g of di-2-ethylhexyl maleate, 25 g of di-2-ethylhexyl sulfosuccinate, Na salt (75% in water), 85.5 g of sodium disulfite powder and 190.1 g of water were introduced into a three-necked flask equipped with a reflux condenser, stirrer, thermometer and nitrogen inlet pipe and heated to 102° C. After about 15 minutes, a gentle reflux began and intensified during the reaction. The temperature was kept at 102° C. until the reflux had completely abated. The reaction mixture was then stirred until it was free from sulfite.

Example 1a) (Comparison Example)

The reaction mixture was cooled to 80° C. and 27 g of ethanol were added. The reaction mixture was then cooled to room temperatures. A clear, homogeneous liquid product with an active substance content of around 70% was obtained. The product had a flashpoint of <55° C.

Example 1b) (Comparison Example)

35 g of 1,2-propylene glycol were added to the eaction mixture. The reaction mixture was then cooled room temperature. A clear, homogeneous liquid product with an active substance content of around 70% was obtained. The product had a flashpoint of >55° C.

Example 1c)

360 g of water and 100 g of a block polymer of ethylene oxide and propylene oxide with a molecular weight of around 2,000 and a PO content of 75 mole-% (EO/PO block polymer of 25 moles of PO and 11 moles of EO on propylene glycol) were added to the reaction mixture, followed by cooling to room temperature. A clear, medium-viscosity liquid product with an active substance content of around 50% and a flashpoint of >100° C. was obtained The same result was obtained when the block polymer mentioned above was replaced by an EO/PO block polymer of 30 moles of P0 and 5 moles of EO on propylene glycol.

Example 2 (Comparison Example)

Synthesis of diisodecyl sulfosuccinate with ethanol as co-solvent 533 g of diisodecyl maleate, 50 g of diisodecyl sulfosuccinate Na salt, 132 g of sodium disulfite powder, 190 g of water and 95 g of ethanol were introduced into a three-necked flask equipped with a reflux condenser, stirrer, thermometer and nitrogen inlet pipe. The mixture was heated to 85° C., initiating a reflux. When the reflux had become weaker, the temperature was increased to 90° C. in several steps. The reaction mixture was stirred at that temperature until the reflux abated. The reaction mixture was then stirred until it was free from sulfite and cooled to room temperature.

A clear, homogeneous liquid product with an active substance content of around 70% was obtained. The product had a flashpoint of <55° C.

Example 3 (Comparison Example)

Synthesis of diisodecyl sulfosuccinate without ethanol as co-solvent 533 g of diisodecyl maleate, 50 g of diisodecyl sulfosuccinate, Na salt, 132 g of sodium disulfite powder and 185 g of water were introduced into the same apparatus as in Example 2. The mixture was heated to 102° C., resulting in a reflux and vigorous foaming. The reaction was continued at 98° C. After a reaction time of about 3 hours, the viscosity of the reaction mixture had increased to such an extent that it could no longer be stirred. After cooling, an incompletely reacted solid product was present and could only be slowly dissolved by addition of 500 ml of ethanol.

Example 4

Synthesis of diisodecyl sulfosuccinate in the presence of a water-soluble polymer of the EO/PO block polymer type as co-solvent 87.8 g of diisodecyl maleate, 15 g of diisodecyl sulfosuccinate Na salt, 21.7 g of sodium disulfite powder, 52 g of water and 30 g of an EO/PO block polymer (molecular weight approx. 2,000, PO content 75 mole-% (EO/PO block polymer of 25 moles of PO and 11 moles of EO on propylene glycol) were introduced into the same apparatus as in Example 1. The mixture was heated to 102° C. A gentle reflux began after about 30 minutes. The reaction was continued at 103° C. After a reaction time of about 5 hours, the reflux abated. The reaction mixture was then stirred at a constant temperature until it was free from sulfite. It was then cooled to room temperature.

A clear, homogeneous liquid product with an active substance content of around 75% was obtained. The product had a flashpoint of >100° C. The same result was obtained when the block polymer mentioned above was replaced by an EO/PO block polymer of 30 moles of PO and 5 moles of EO on propylene glycol.

We claim:

1. A liquid composition consisting of
A) at least one sulfosuccinic diester of the formula:

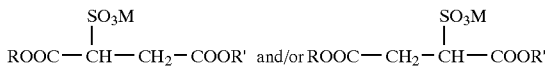

in which M is an inorganic or organic cation, R and R' independtly of one another represent aliphatic or cycloaliphatic $C_{3\text{-}22}$ alkyl, $C_{2\text{-}22}$ alkenyl or optionally $C_{1\text{-}8}$ alkyl-substituted $C_{6\text{-}22}$ aryl;

B) water as a solvent; and

C) a cosolvent consisting of at least one polymer containing alkylene oxide units which is liquid at 10° C.

2. The liquid composition of claim 1 wherein component C) is present in from about 1 to about 40% by weight, based on the weight of component A).

3. The liquid composition of claim 2 wherein component C) is present in from about 5 to about 20% by weight.

4. The liquid composition of claim 2 wherein component A) is present in from about 30 to about 70% by weight, based on the weight of the composition.

5. The liquid composition of claim 3 wherein component A) is present in from about 30 to about 60% by weight, based on the weight of the composition.

6. The composition of claim 1 wherein component C) is selected from the group consisting of a block polymer of ethylene oxide (EO) and propylene oxide (PO), and an adduct of EO and/or PO with a monofunctional or polyfunctional alcohol.

7. The composition of claim 6 wherein said polyfunctional alcohol is ethylene glycol or propylene glycol.

8. The composition of claim 6 wherein the block polymer of EO and PO has a percentage PO content of at least 20 mole-%.

9. The composition of claim 8 wherein the block polymer of EO and PO has a molecular weight of from about 500 to about 20,000.

10. The composition of claim 1 wherein component A) is didecyl sulfosuccinate, diisodecyl sulfosuccinate, di-2-ethylhexyl sulfosuccinate or diisotridecyl sulfosuccinate.

11. The composition of claim 1 wherein M is lithium, sodium, potassium, or ammonium.

12. The composition of claim 9 wherein the block polymer has a molecular weight of from about 500 to about 5,000.

13. A process for the preparation of the liquid composition of claim 1 comprising the steps of I) reacting a maleic acid diester corresponding to the formula ROOC—CH=CH—COOR', where R and R' independently of one another represent aliphatic or cycloaliphatic $C_{3-22}$ alkyl, $C_{2-22}$ alkenyl or optionally $C_{1-8}$-alkyl-substituted $C_{6-22}$ aryl, with a sulfiting agent in the presence of components B) and C) of claim 16 at a temperature in the range of from about 60 to about 150° C., optionally under supraatmospheric pressure; and II) cooling the resulting reaction mixture.

14. The process of claim 13 wherein the molar ratio of maleic acid diester to sulfiting agent, based on $HSO^-_3$ is from about 1:09 to about 1:2.

15. The process of claim 13 wherein the sulfiting agent is $MHSO_3$, $M_2SO_3$ or $M_2S_2O_5$, where M is an inorganic or organic cation.

16. The process of claim 13 wherein from about 0.1 to about 20% by weight of the sulfosuccinic acid diester produced by the process is added to the reaction mixture in step I) as a reaction initiator.

17. The process of claim 14 wherein said molar ratio is from about 1:1 to about 1:1.2.

18. A process for the preparation of the liquid composition of claim 1, wherein R and R' in the sulfosuccinic acid diester independently represent a $C_{3-8}$ alkyl group, comprising the steps of I) reacting a maleic acid diester of the formula ROOC—CH=CH—COOR', where R and R' independently represent a $C_{3-8}$ alkyl group, with a sulfiting agent in the presence of water as a solvent at a temperature in the range of from about 60 to about 150° C., optionally under supraatmospheric pressure;

II) adding to the hot reaction mixture from step I) component C) of claim 16; and III) cooling the hot reaction mixture.

19. The process of claim 18 wherein the molar ratio of maleic acid diester to sulfiting agent, based on $HSO^-_3$, is from about 1:0.9 to about 1:2.

20. The process of claim 18 wherein from about 0.1 to about 20% by weight of the sulfosuccinic acid diester produced by the process is added to the reaction mixture step I) as a reaction initiator.

21. A liquid composition consisting of

A) from about 30 to about 70% by weight, based on the weight of the composition, of at least one sulfosuccinic acid diester of the formula:

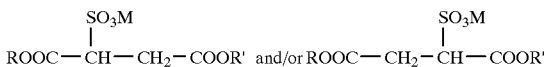

in which M is an inorganic or organic cation, R and R' independently of one another represent aliphatic or cycloaliphatic $C_{3-22}$ alkyl, $C_{2-22}$ alkenyl or optionally $C_{1-8}$ alkyl-substituted $C_{6-22}$ aryl;

B) water as a solvent; and

C) from about 1 to about 40% by weight, based on the weight of component A), of at least one cosolvent liquid at 10° C. selected from the group consisting of a block polymer of ethylene oxide (EO) and propylene oxide (PO), and an adduct of EO and/or PO with a monofunctional or poly-functional alcohol.

22. The liquid composition of claim 21 wherein component A) is present in from about 30 to about 60% by weight, based on the weight of the composition, and wherein component C) is present from about 5 to about 20% by weight.

23. The composition of claim 21 wherein in component C) said polyfunctional alcohol is ethylene glycol or propylene glycol.

24. The composition of claim 21 wherein in component C) the block polymer of EO and PO has a percentage PO content of at least 20 mole-%.

25. The composition of claim 24 wherein the block polymer of EO and PO has a molecular weight of from about 500 to about 20,000.

26. The composition of claim 21 wherein component A) is didecyl sulfosuccinate, diisodecyl sulfosuccianate, di-2-ethylhexyl sulfosuccinate or diisotridecyl sulfosuccinate.

27. The compostion of claim 21 wherein M is lithium, sodium, potassium, or ammonium.

* * * * *